(12) United States Patent
Sugiyama et al.

(10) Patent No.: US 8,211,077 B2
(45) Date of Patent: Jul. 3, 2012

(54) DISPOSABLE PANT-TYPE DIAPER

(75) Inventors: Katsuhiko Sugiyama, Tokyo (JP); Tomotsugu Miyoshi, Kawagoe (JP); Takeshi Niimi, Tottori (JP); Izumi Tashiro, Kasugai (JP); Kahori Suzuki, Saitama (JP)

(73) Assignees: Oji Nepia Co., Ltd., Tokyo (JP); Oji Paper Co., Ltd., Tokyo (JP)

( * ) Notice: Subject to any disclaimer, the term of this patent is extended or adjusted under 35 U.S.C. 154(b) by 842 days.

(21) Appl. No.: 11/918,007

(22) PCT Filed: Mar. 31, 2006

(86) PCT No.: PCT/JP2006/306875
§ 371 (c)(1),
(2), (4) Date: Oct. 5, 2007

(87) PCT Pub. No.: WO2006/109596
PCT Pub. Date: Oct. 19, 2006

(65) Prior Publication Data
US 2009/0036860 A1 Feb. 5, 2009

(30) Foreign Application Priority Data
Apr. 11, 2005 (JP) .................................. 2005-113584

(51) Int. Cl.
*A61F 13/15* (2006.01)
*A61F 13/20* (2006.01)
(52) U.S. Cl. ............. 604/385.29; 604/385.25; 604/385.3
(58) Field of Classification Search ............. 604/385.29, 604/385.3, 385.25
See application file for complete search history.

(56) References Cited

U.S. PATENT DOCUMENTS

| | | | | |
|---|---|---|---|---|
| 4,568,344 A | * | 2/1986 | Suzuki et al. | 604/389 |
| 4,850,988 A | * | 7/1989 | Aledo et al. | 604/385.21 |
| 5,370,634 A | * | 12/1994 | Ando et al. | 604/385.21 |
| 5,690,626 A | * | 11/1997 | Suzuki et al. | 604/385.25 |
| 5,693,038 A | * | 12/1997 | Suzuki et al. | 604/385.23 |
| 5,746,731 A | | 5/1998 | Hisada | |
| 5,827,260 A | * | 10/1998 | Suzuki et al. | 604/385.24 |
| 5,904,793 A | | 5/1999 | Gorman et al. | |

(Continued)

FOREIGN PATENT DOCUMENTS

JP  U 5-39531  5/1993

(Continued)

OTHER PUBLICATIONS

Office Action issued in Taiwanese Patent Application No. 95111606 on Mar. 23, 2010 (with English translation).

*Primary Examiner* — Tatyana Zalukaeva
*Assistant Examiner* — Ginger T Chapman
(74) *Attorney, Agent, or Firm* — Oliff & Berridge, PLC

(57) ABSTRACT

A disposable pant-type diaper according to the present invention includes a front portion, a back portion, and a crotch portion which is positioned between the front and back portions, in which a waist opening and a pair of leg openings are formed by joining both longitudinal side-edge portions of the front and back portions which face each other, and stretchable elastic members are disposed along at least a part of each opening, wherein a cutout portion is formed in at least a portion of the side-edge portion of at least one of the front and back portions, and the front and back portions assume a non-joining state at the portion where the cutout portion is formed.

14 Claims, 8 Drawing Sheets

U.S. PATENT DOCUMENTS

| | | | |
|---|---|---|---|
| 6,491,676 B1 * | 12/2002 | Suzuki et al. | 604/385.29 |
| 6,726,670 B2 * | 4/2004 | Almberg et al. | 604/392 |
| 7,722,591 B2 * | 5/2010 | Back | 604/385.31 |
| 7,959,619 B2 * | 6/2011 | Cartier et al. | 604/385.01 |
| 8,020,523 B2 * | 9/2011 | Ikegami et al. | 119/869 |
| 2001/0016720 A1 | 8/2001 | Otsubo | |

FOREIGN PATENT DOCUMENTS

| | | |
|---|---|---|
| JP | A 5-317356 | 12/1993 |
| JP | U 7-7621 | 2/1995 |
| JP | A 8-294510 | 11/1996 |
| JP | A 10-503096 | 3/1998 |
| JP | A 2003-144493 | 5/2003 |
| JP | A 2003-533247 | 11/2003 |
| JP | A 2004-329238 | 11/2004 |
| JP | A 2004-350864 | 12/2004 |
| JP | A 2005-058396 | 3/2005 |
| JP | A 2005-131131 | 5/2005 |
| TW | 344654 | 11/1988 |
| TW | 530635 | 5/2003 |

* cited by examiner

DISPOSABLE PANT-TYPE DIAPER

TECHNICAL FIELD

The present invention relates to a disposable pant-type diaper, and more particularly to a disposable pant-type diaper which can prevent a waist portion from becoming sweaty when a wearer wears the diaper and also can facilitate the removal of the diaper from the wearer after use.

BACKGROUND ART

A disposable pant-type diaper is a pull-on type disposable diaper, and is also called a pull-on disposable diaper. In general, a main body of the disposable pant-type diaper comprises a liquid permeable top sheet, a liquid impermeable back sheet and an absorbent member which is disposed between both the sheets. In forming the pant-type disposable diaper using this main body, both side-edges of front and back portions of the main body which face each other are joined together thus forming a waist opening and a pair of leg openings. Then, a stretchable elastic member is arranged along each opening. With respect to the disposable pant-type diaper, various types of diapers have been proposed to enable the proper use of the diaper depending on the usage. Such disposable pant-type diapers have been popularly used not only by infants but also by adult incontinence persons.

In the disposable pant-type diaper, by enhancing the fitting property of the waist opening and the leg openings, the enhancement of a leak prevention effect is realized. However, when a waist size or a thigh size of the wearer is smaller than a waist size or a thigh size of the diaper, the waist opening or the leg opening of the diaper can not be sufficiently fit on the waist or the leg of the wearer. As the result, there is a possibility that leak is generated from these parts.

Various proposals have been made to overcome the above-mentioned drawbacks. Patent Document 1 discloses a disposable pant-type diaper in which an adjusting tape is arranged along a waist opening and leg openings thus fastening each opening using the adjusting tape. Patent Document 2 discloses a disposable pant-type diaper in which an adjusting tape is arranged along a waist opening thus fastening the waist opening using the adjusting tape. Patent Documents 3 and 4 disclose a disposable pant-type diaper in which a fastening strip is arranged on both side-edges of a waist portion thus fastening the waist portion using the fastening strip.

All of these conventional disposable pant-type diapers can improve a leaking prevention effect by enhancing the fitting property of the waist portion and the leg portion. Accordingly, the diaper covers an excessively large area of a waist portion of the wearer. As a result, there exists a drawback that a part of the wearer ranging from the waist portion to the leg portion is liable to become easily sweaty.

In removing the disposable pant-type diaper from the wearer after use, it is necessary to remove the diaper by tearing joining portions at the side-edge portions which join the front and back portions with hands. However, with respect to a conventional disposable pant-type diaper, depending on the joining state of the side-edge portion, there may be a case that it is difficult to tear with hands. Accordingly, at the time of tearing the joining portion of the diaper, an excessive force is applied to the diaper and hence, wastes are stuck out from the diaper and smears clothing or skin of the wearer.

It is an object of the present invention to overcome the drawbacks which the above-mentioned conventional disposable pant-type diaper possesses. To be more specific, it is an object of the present invention to provide a disposable pant-type diaper which gives a comfortable wearing feeling by preventing sweating of the waist portion at the time of wearing the diaper and, at the same time, facilitates the tearing of the joining portion of the side-edge portions of front and back portions even at the time of removing the diaper from the wearer after use.

Patent Document 1: Japanese Utility Model Application Laid-open No. Hei 5-39531
Patent Document 2: Japanese Patent Application Laid-open No. Hei 10-503096
Patent Document 3: Japanese Patent Application Laid-open No. Hei 5-317356
Patent Document 4: Japanese Patent Application Laid-open No. 2003-533247

DISCLOSURE OF THE INVENTION

A disposable pant-type diaper according to the present invention comprises a front portion, a back portion, and a crotch portion which is positioned between these front and back portions, wherein a waist opening and a pair of leg openings are formed by joining both longitudinal side-edge portions of the front and back portions which face each other, and a stretchable elastic member is disposed along at least a part of each opening and at least one cutout portion is formed in the side-edge portion of at least one of the front and back portions, and the front and back portions assume a non-joining state at the portion where the cutout portion is formed.

According to the disposable pant-type diaper of the present invention, since the front and back portions assume a non-joining state at the part where the cutout portion is formed, the diaper has favorable air permeability and hence, it is possible to prevent the sweatiness of the waist portion when wearing. Further, when the diaper is removed from the wearer by tearing the diaper at the joining portion after use, since a joining portion is not formed at the cutout portion, a joining region is shorter than the joining region of the conventional diaper and hence, it is possible to facilitate to tear the joining portion.

As a stretchable elastic member which is disposed along at least a part of the opening in the present invention, a stretchable elastic member which is used for a usual disposable diaper such as a string rubber or a flat rubber made of a natural rubber or synthetic rubber e.g. urethane and so on can be used. These stretchable elastic members are arranged in a stretched state and fixed by adhesion using hot-melt adhesive or the like so as to be used members.

In the disposable pant-type diaper according to the present invention, on the portion where the cutout portion is formed in one portion out of the front and back portions, it is possible to attach an adjusting tape having fastening means which is detachably fastened with respect to the other portion. In this case, it is preferable that a base material of the adjusting tape is made of a material having a stretchable elasticity. For example, a sheet which is formed by sandwiching and fixing a stretching film, a flat rubber, a string rubber or the like with a nonwoven fabric, a stretchable foam or the like may be adopted. Further, as the fastening means, various types of adhesive, a hook element or a loop element of a hook-and-loop fastener may be adopted.

In this manner, by attaching the adjusting tape having the fastening means, the portion where the cutout portion is formed is fastened using the adjusting tape so as to realize favorable fitting property at this portion.

The disposable pant-type diaper according to the present invention may be a so-called all-in-one-type pull-on disposable diaper which comprises a main body having a liquid permeable top sheet, a liquid impermeable back sheet, and an absorbent member which is arranged between the both sheets, the diaper being formed into a panties shape by joining both side-edge portions of the front and back portions of the main body which face each other. In this case, it is possible that side panels are attached on both side-edge portions of the front and back portions of the main body, and the side panels are joined to each other thus forming the main body into a panties shape. These side panels can be formed of a material having a stretchable elasticity.

As a liquid permeable top sheet, it is possible to use a nonwoven fabric to which a hydrophilic treatment is applied. The nonwoven fabric may be made of a synthetic fiber or the like using a thermoplastic resin such as polyethylene, polypropylene, polyester or other resin as a raw material.

As a liquid impermeable back sheet, preferably, a liquid impermeable sheet having the vapor permeability such as a polyethylene sheet in which micro pores are made or a sheet formed by drawing the thermoplastic resin added with filler is used.

As an absorbent member, it is possible to use any absorbent member provided that the absorbent member can be used in absorbing articles such as a usual disposable diaper. That is, it is preferable to use an absorbent member in which flocculent pulp and super-absorbent polymer (SAP) are used in combination and, further, an absorbent member to which thermal adhesiveness fibers is added, and the whole absorbent member is covered with a sheet having hydrophilic property such as a tissue. In addition, it is also possible to use a sheet-like absorbent member in which a SAP layer is formed on one surface of a sheet having a hydrophilic property or in which a SAP is sandwiched between two sheets having the hydrophilic property.

With respect to a side panel, it is possible to form the side panel using thermal adhesiveness nonwoven fabric formed of a synthetic fiber using thermoplastic resin such as polyethylene, polypropylene, polyester or other resin as a raw material. It is possible to use a sheet in which a stretchable elastic member such as a stretchable film, a stretchable net, flat rubber, string rubber, stretchable foam is fixed on this nonwoven fabric by adhesion in a stretching state using hot-melt adhesive or a sheet which is fixed by sandwiching between nonwoven fabrics using thermal bonding. It is also possible to use a sheet which is made stretchable by sandwiching and fixing a stretchable elastic member with a natural length between stretchable nonwoven fabrics.

The disposable pant-type diaper according to the present invention may be a so-called two-piece type pull-on disposable diaper which comprises a main absorbent body having a liquid permeable top sheet, a liquid impermeable back sheet, and an absorbent member which is arranged between the both sheets, and a belt-like connecting member which is arranged between the front and rear portion of the main absorbent body and has a length extending outside from the both side-edge portions of the main absorbent body, the diaper being formed into a panties shape by joining both side-edge portions of the connecting members which face each other along a longitudinal direction of the diaper. In this case, the belt-like connection portion may be formed of a material having a stretchable resiliency.

The connecting member can be formed of a nonwoven fabric containing synthetic fabric using a thermal adhesiveness resin such as polyethylene, polypropylene, polyester or other resin as a raw material. Such a nonwoven fabric is formed of a fiber constituted of any one of the above-mentioned raw material synthetic fibers or the mixture of two or more kinds of core-in-sheath fiber using two kinds of synthetic resin raw material. This nonwoven fabric may be manufactured from a mixed raw material of thermal adhesiveness synthetic fibers and other natural fibers or synthetic fibers. With respect to the connecting member, these nonwoven fabrics can be used in a single sheet or in a state that two or more sheets are layered or, further, one sheet of nonwoven fabric can be used in a folded state.

The disposable pant-type diaper according to the present invention may be a so-called two-piece type pull-on disposable diaper which comprises a main absorbent body having a liquid permeable top sheet, a liquid impermeable back sheet, and an absorbent member which is arranged between the both sheets, and an outer member on which this main absorbent body is attached and holds the main absorbent body so that the main absorbent body is brought into contact with a wearer, wherein both side-edge portions of the front and rear portions of the outer member which face each other are joined so that the diaper is formed into a panties shape.

In this case, as an outer member, it is possible to use a non-woven fabric made of a synthetic fiber using a thermoplastic resin such as polyethylene, polypropylene, polyester or other resin as a raw material, and these nonwoven fabric can be used in any one or two or more of nonwoven fabrics can be used in a laminating manner.

The above-mentioned and other objects, effects, features and advantages of the present invention will be made further apparent using following embodiments taken in conjunction with attached drawings.

BRIEF DESCRIPTION OF THE DRAWINGS

FIG. 2 is assembled;

BEST MODES FOR CARRYING OUT THE INVENTION

Hereinafter, a disposable pant-type diaper of the present invention is explained in conjunction with drawings. It is needless to say that the present invention is not limited by these embodiments at all.

Figure 1:
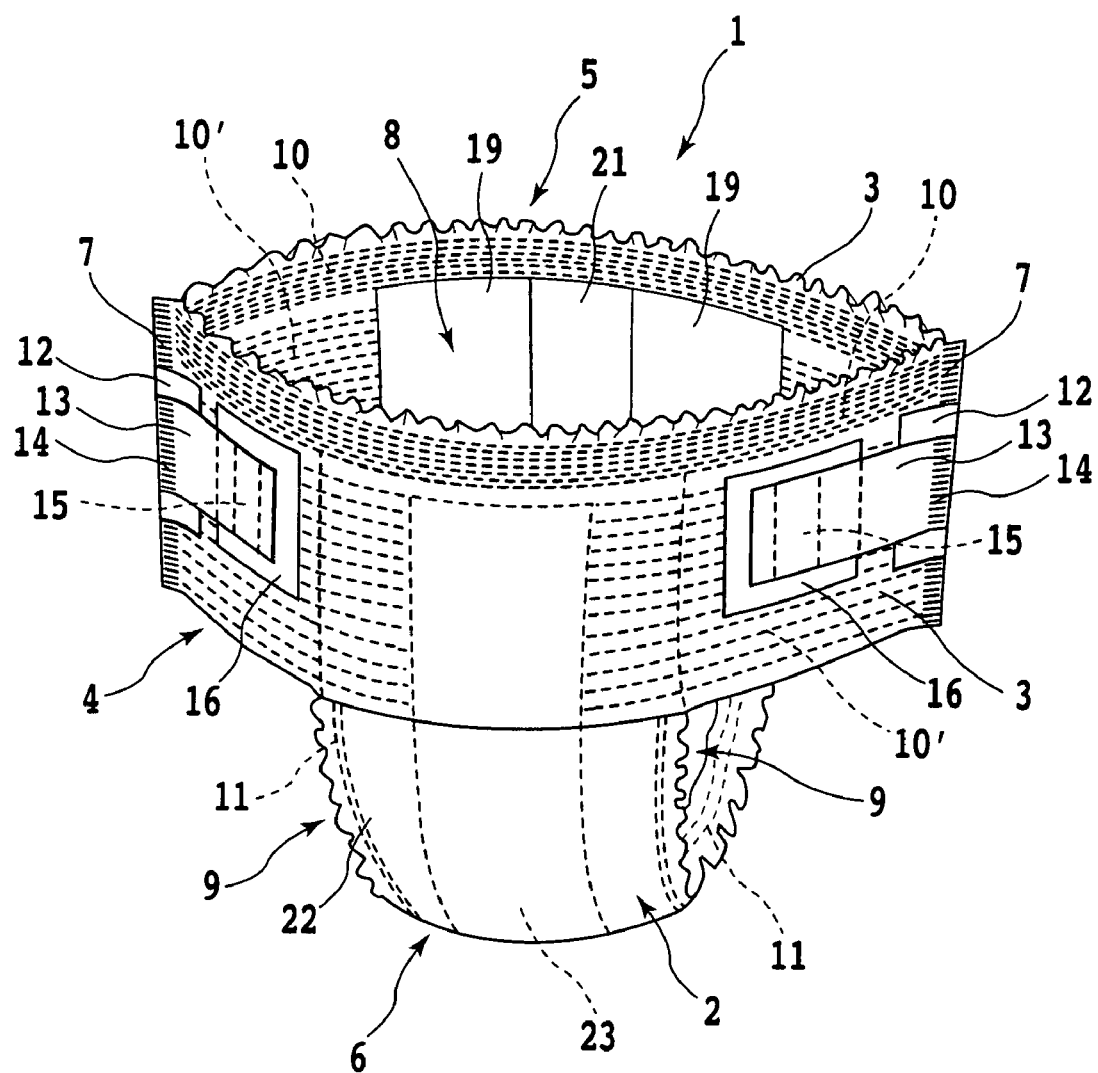
FIG. 1 is a perspective view of a disposable pant-type diaper of one embodiment of the present invention as viewed from a front portion side.

The appearance of one embodiment of a disposable pant-type diaper according to the present invention is shown in FIG. 1. FIG. 1 is a perspective view showing a state in which the disposable pant-type diaper is assembled as viewed from a front portion side.

In FIG. 1, the disposable pant-type diaper 1 includes a main absorbent body 2 and belt-like connecting members 3 which are mounted in regions on both longitudinal end portions of the main absorbent body 2. The main absorbent body 2 is folded at a crotch portion 6 and longitudinal side-edge portions of the connecting members 3 of the front portion 4 and the back portion 5 along the longitudinal direction of the diaper are joined to each other by way of joining portions 7. Due to such a constitution, a waist opening 8 and a pair of leg openings 9 are formed. Stretchable elastic members 10, 11 are arranged along the respective openings. Further, a plurality of stretchable elastic members 10' are also arranged along the widthwise direction of the diaper on the portions of loins where the main absorbent body 2 is not present.

A cutout portion 12 is formed in both longitudinal side-edge portions of the connecting member 3 on the front portion 4 side. The portion of the longitudinal side-edge portion where the cutout portion 12 is formed is not joined to the connecting member 3 of the back portion 5 side, that is, the cutout portion 12 is in a non-joining state with respect to the connecting member 3 of the back portion 5 side. An adjusting tape 13 is arranged on the portion where the cutout portion 12 is formed. One end portion of the adjusting tape 13 is joined to the side-edge portion of the connecting member 3 on the back portion 5 side by way of a joining portion 14, while a fastening means 15 is attached on another edge region of the adjusting tape 13. The fastening means 15 is detachably fastened to a target sheet 16 which is arranged on a surface of the connecting member 3 of the front portion 4 side.

In this embodiment, the connecting member 3 may be formed of a non-woven fabric which contains synthetic fibers which uses a thermal adhesiveness resin such as polyethylene, polypropylene, polyester or other resin as a raw material thereof. Such non-woven fabric may be formed of fibers made of a single body of the above-mentioned raw-material synthetic fibers or the fibers into which one kind out of plural kinds of core-in-sheath fibers which use two kinds of synthetic resin raw materials are mixed. The non-woven fabric may be manufactured from a mixture material of thermal adhesiveness synthetic fibers and other natural fibers or synthetic fibers.

In this embodiment, as the stretchable elastic members 10, 10', 11 which are arranged on the connecting members 3, the waist opening 8 and the leg openings 9, the stretchable elastic members made of natural or synthetic urethane threads, string rubber, flat rubber or the like which are used in a usual disposable diaper can be used without modification. These stretchable elastic members 10, 10', 11 are arranged in a stretched state and, thereafter, adhered and fixed using a hot melt adhesive agent or the like.

In this embodiment, the adjusting tape 13 is formed by arranging the fastening means 15 on one edge region of a base sheet.

Since there exists a possibility that the base sheet comes into contact with a skin of a wearer, it is preferable to form the base sheet using a flexible material having stretching property. To be more specific, it is possible to adopt a sheet which is formed by sandwiching and fixing a stretching film, flat rubber, string rubber or the like between non-woven fabrics or a stretchable foamed body. As the fastening means 15, various adhesive agents or hook elements or loop elements of a hook-and-loop fastener may be used.

In this embodiment, when the fastening means 15 is formed of an adhesive agent, as the target sheet 16 which is detachably fastened to the fastening means 15 of the adjusting tape 13, a film which is made of various kinds of synthetic resins which can be re-adhered with and re-peeled from the adhesive agent is used. When the fastening means 15 is formed of the hook elements of the hook-and-loop fastener, the loop elements which are engageable with the hook elements or a non-woven fabric can be used as the target sheet 16.

In this manner, in this embodiment, the target sheet 16 which can be fastened to the fastening means 15 of the adjusting tape 13 is arranged on the surface of the connecting member 3 on the front portion 4 side. However, when the connecting member 3 is formed of a material which can be fastened to the fastening means 13, it is unnecessary to arrange the target sheet 16.

Figure 2:
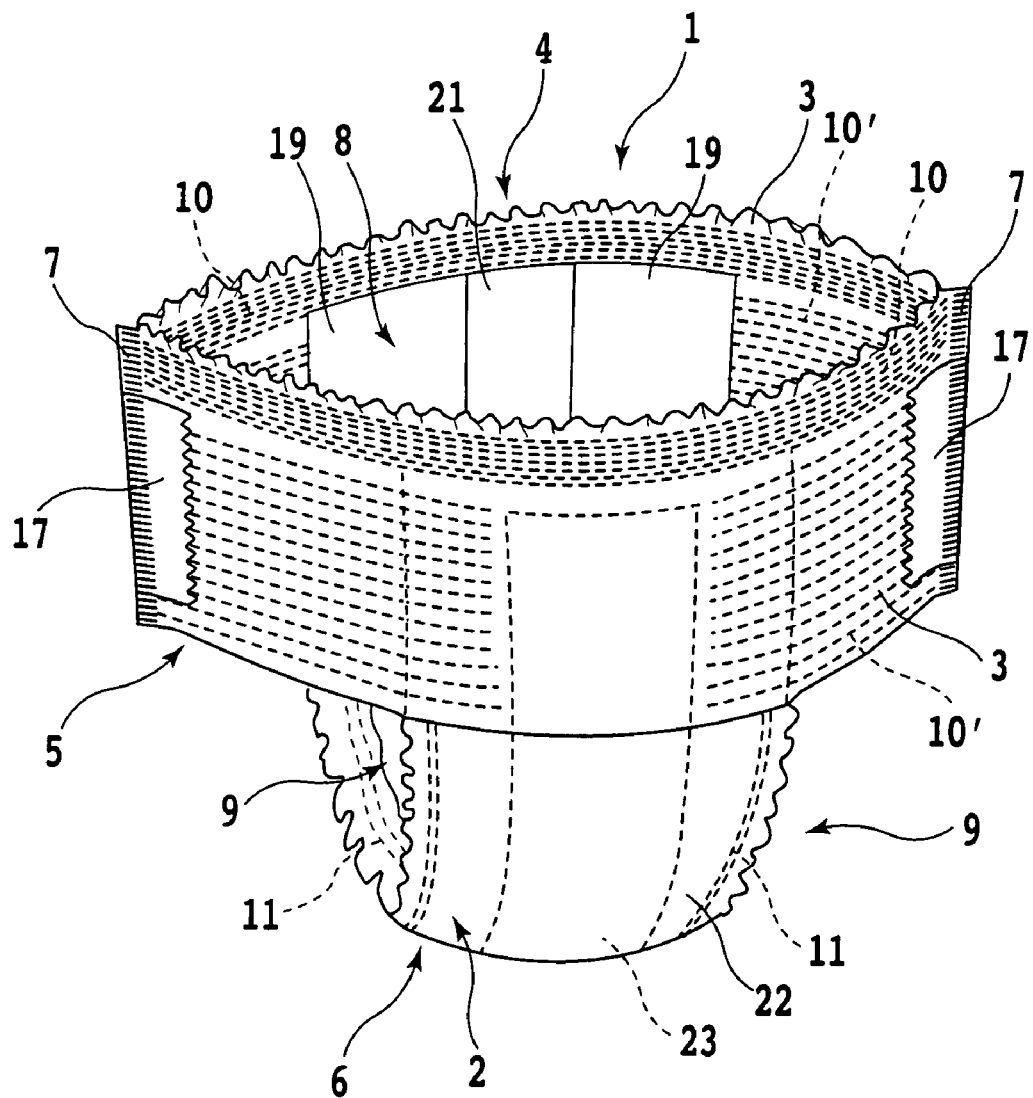
FIG. 2 is a perspective view of the disposable pant-type diaper in FIG. 1 as viewed from a back portion side.

FIG. 2 is a perspective view of the disposable pant-type diaper shown in FIG. 1 as viewed from the back portion 5 side.

In FIG. 2, on surfaces of both longitudinal side-edge portions of the connecting member 3 on the back portion 5 side of the disposable pant-type diaper 1, reinforcement sheets 17 are arranged and are joined to the connecting member 3 by way of the joining portions 14. By arranging the reinforcement sheets 17 in this manner, as shown in FIG. 1, when the adjusting tapes 13 are arranged on portions of the cutout portions 12, it is possible to firmly join the adjusting tapes 13 to the connecting member 3 on the back portion 5 side together with the reinforcement sheets 17. As a result, a wearer can easily perform the manipulation to pull the adjusting tapes 13 so as to tighten the portions where the cutout portions 12 are formed.

The reinforcement sheets 17 of this embodiment may be formed of a thermal adhesiveness non-woven fabric made of synthetic fibers which use polyethylene, polypropylene, polyester or other thermoplastic resin as a raw material. A basis weight of the non-woven fabric is preferably 20 to 100 g/m$^2$, and is more preferably 40 to 70 g/m$^2$.

In the embodiment shown in FIG. 1 and FIG. 2, the stretchable elastic members 10' are arranged on the trunk part in a discontinuous state such that the stretchable elastic members 10' are not arranged on portions where the main absorbent body 2 is present. However, the stretchable elastic members 10' may be arranged over the whole trunk part in a continuous state.

Figure 3:
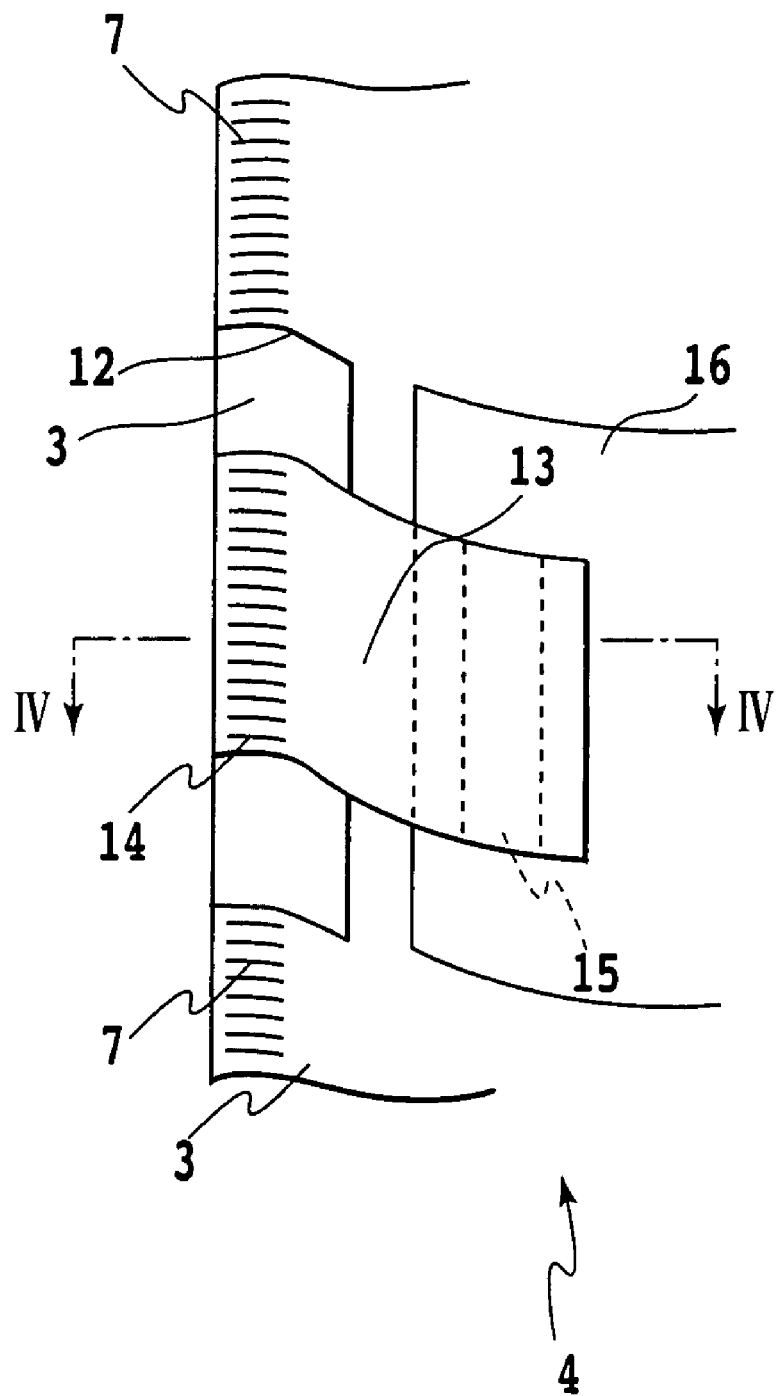
FIG. 3 is an enlarged perspective view of one cutout portion which are formed in side-edge portions of front and back portions of the disposable pant-type diaper shown in FIG. 1.

FIG. 3 is a partially enlarged plan view showing a state of a portion where the cutout portions 12 are formed on the side edge portions of the front and back portions 4, 5.

In FIG. 3, the cutout portion 12 is formed on the side-edge portion of the connecting member 3 on the front portion 4 side. In the portion where the cutout portion 12 is formed, the connecting members 3 on the front portion 4 side and the back portion 5 side are held in a non-joining state. The adjusting tape 13 is arranged on the portion of the connecting member 3 where the cutout portion 12 is formed. One end portion of the adjusting tape 13 is joined to the side edge portion of the connecting member 3 on the back portion 5 side by way of the joining portion 14. The fastening means 15 is attached on another edge region of the adjusting tape 13. The fastening means 15 is detachably fastened to the surface of the connecting member 3 on the front portion 4 side.

Figure 4:
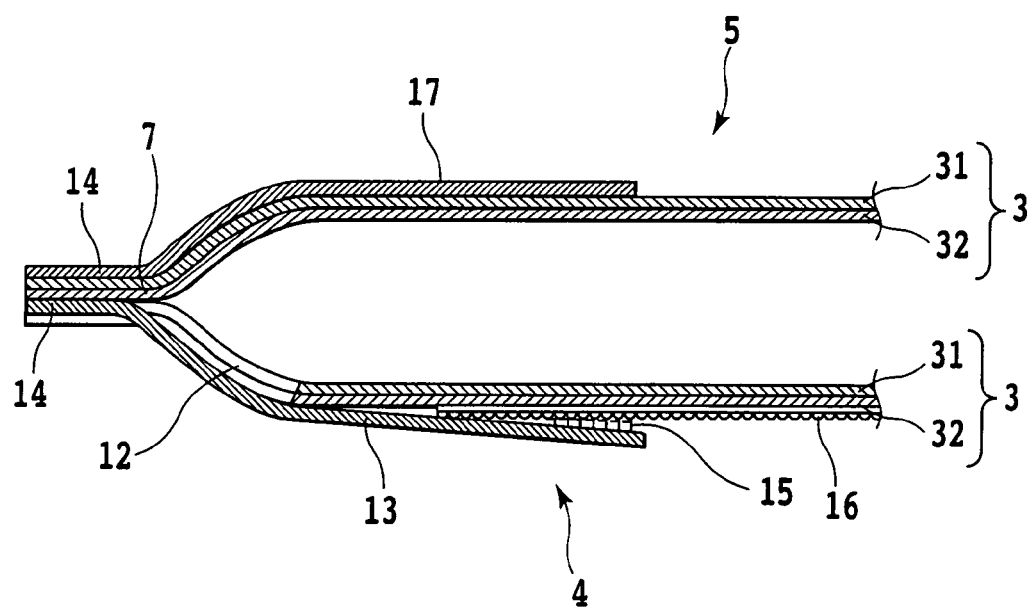
FIG. 4 is a cross-sectional view taken along a line IV-IV in FIG. 3.

FIG. 4 is a cross-sectional view taken along a line IV-IV in FIG. 3.

In FIG. 4, the connecting member 3 includes two sheets of non-woven fabrics 31, 32, wherein the previously mentioned stretchable elastic member 10' is sandwiched between these non-woven fabrics 31, 32.

At the portion of the cutout portion 12 which is formed in the side edge portion of the connecting member 3 on the front portion 4 side, the connecting members 3 on the front portion 4 side and the back portion 5 side are held in a non-joining state. The adjusting tape 13 is arranged on the portion where the cutout portion 12 is formed. One end portion of the adjusting tape 13 is joined by way of the joining portion 14 together with the reinforcement sheet 17 which are arranged on the side-edge portion of the connecting member 3 on the back portion 5 side and a surface of the connecting member 3. On another end region of the adjusting tape 13, hook elements forming one side of the hook-and-loop fastener which constitute the fastening means 15 are attached. The hook elements are detachably fastened to the target sheet 16 on the connecting member 3 on the front portion 4 side.

In this manner, in the disposable pant-type diaper 1 of this embodiment, in the portion where the cutout portion 12 is formed, the adjusting tape 13 having the fastening means 15 which is detachably fastened with the other portion is attached on either one of the front portion 4 or the back portion 5. Accordingly, by tightening the portion where the cutout portion 12 is formed with the adjusting tape 13, it is possible to improve the fitting feeling of this portion. As a result, the diaper having the above-mentioned constitution is useful as a disposable pant-type diaper 1 not only for infants but also for adult incontinence persons.

The disposable pant-type diaper 1 of this embodiment is formed by joining both longitudinal side edge portions of the front portion 4 and the back portion 5 which face each other. At least one cutout portion 12 is formed in the side edge portion of at least one of the bodies. At a portion where the cutout portion 12 is formed, the front portion 4 and the back portion 5 are held in a non-joining state. That is, in the disposable pant-type diaper 1 of this embodiment, the front and back portions 4, 5 are held in the non-joining state at the portion where the cutout portions 12 are formed and hence, permeability to air is enhanced so that the sweating of the waist part at the time of wearing the diaper can be prevented. Further, when the diaper is removed from the wearer by tearing the diaper at the joining portion 7 after use, because it is possible to easily tear the diaper the joining portion 7 is not formed in the portion of the cutout portion 12 and, a length of the joining portion 7 is small.

Figure 5:
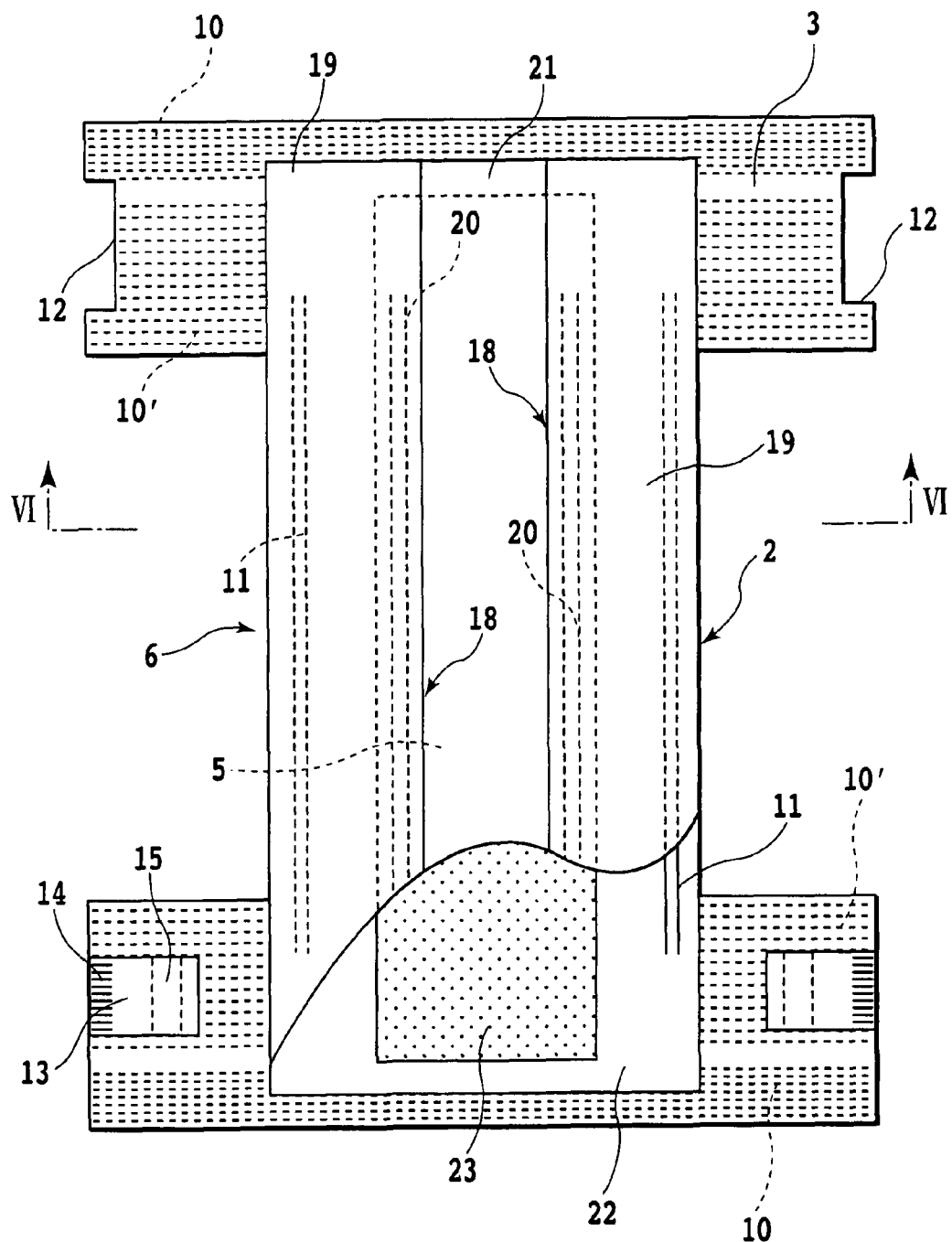
FIG. 5 is a developed plan view with a part broken away as viewed from a top sheet side showing a state before the disposable pant-type diaper shown in FIG. 1
Figure 6:
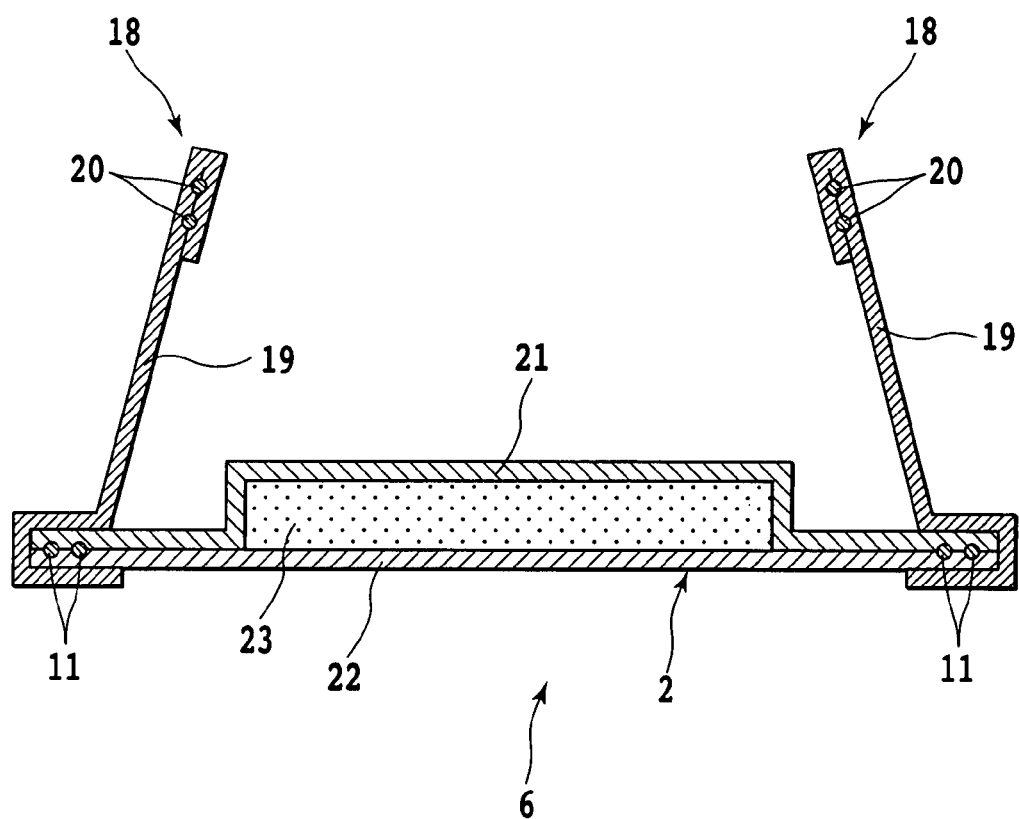
FIG. 6 is a cross-sectional view taken along a line VI-VI in FIG. 5.

FIG. 5 shows a state of the disposable pant-type diaper of this embodiment before the diaper is assembled, and FIG. 6 shows the cross-sectional structure as viewed in the direction indicated by VI-VI. FIG. 5 is a developed plan view with a part broken away of the disposable pant-type diaper as viewed from the top sheet side.

In FIG. 5 and FIG. 6, the disposable pant-type diaper 1 includes a main absorbent body 2 and a belt-like connecting member 3. Main elements of the main absorbent body 2 include a liquid permeable top sheet 21, a liquid impermeable back sheet 22, and an absorbent member 23 which is arranged between the both sheets. The connecting member 3 has, in a front portion 4 and a back portion 5 of the main absorbent body 2, a length larger than a width of the main absorbent body 2 and extends outwardly from both side edge portions of the main absorbent body 2.

A waist stretchable elastic member 10 is arranged at a position of a waist opening 8 of longitudinal edge portions of the connecting member 3, while loin stretchable elastic member 10' is arranged at a position of loins. A cutout portion 12 is formed on both longitudinal side-edge portions of the connecting member 3 on the front portion 4 side. Leg stretchable elastic members 11 are arranged at positions of leg openings 9 at both side-edge portions of a crotch portion 6 of the main absorbent body 2. Inside the leg stretchable elastic member 11, a pair of stand-up gathers 18 which extend along the longitudinal direction of the diaper is formed. The stand-up gathers 18 according to the embodiment includes a pair of seats 19 which is attached on the outer side edge portions of the top seat 21 and the back seat 22 so that the edge portions of the top seat 21 and the back seat 22 are enclosed with each outer side edge portion of the seats 19.

The stand-up gather 18 which is raised from an inner surface of the main absorbent body 2 may be formed of various kinds of materials. For example, the sheet 19 of the stand-up gather 18 may be formed using an air permeable and water-repellant non-woven fabric made of synthetic fibers which uses thermoplastic resin such as polyethylene, polypropylene, polyester or the like as a raw material. Alternatively, using an non-woven fabric having a large width and forming side flaps, the side flaps are formed and, at the same time, the stand-up gather 18 may be formed by a portion which extends toward the inside of the diaper. Further, it may be possible to use the top sheet 21 having a large width thus forming the stand-up gather 18 using portions which extend from both side edges of the absorbent member 23 of the top sheet 21.

Further, at least one stretchable elastic member 20 is arranged on a side edge portion of a free portion of the stand-up gather 18. As the stretchable elastic member, the stretchable elastic members made of natural or synthetic urethane threads, string rubber, flat rubber or the like which are used in a usual disposable diaper can be directly used without modification. These stretchable elastic members are arranged on the side edge portion of the free portion in a stretched state and fixed by adhesion using a hot-melt adhesive or the like.

In this embodiment, a sheet which is obtained by applying the hydrophilic treatment to the non-woven fabric made of synthetic fibers which use polyethylene, polypropylene, polyester or other thermoplastic resin as a raw material is used as the liquid permeable top sheet 21.

As the liquid impermeable and air-permeable back sheet 22, a liquid impermeable sheet having the moisture permeability such as a polyethylene sheet having minute holes or a sheet which is formed by adding filler into a thermoplastic resin and by drawing such resin is used. With the use of such a sheet, the sweating is reduced and hence, the wearer can obtain the comfortable wearing feeling. Further, it is also possible to use the sheet having the stacked structure in which a cover sheet made of a non-woven fabric is laminated to the outside of the sheet.

As the absorbent member 23, any absorbent member which is used in an absorbing article such as a usual disposable diaper can be used. That is, an absorbent member which uses the flocculent pulp and super-absorbent polymer (SAP) in combination, an absorbent member in which thermal adhesiveness fibers are added or the like can be used. Further, it is preferable to use an absorbent member which is wrapped by a hydrophilic sheet. Besides these absorbent bodies, it is possible to use a sheet-like absorbent member such as an absorbent member which has a SAP layer on one side of a hydrophilic sheet such as a tissue, an absorbent member which sandwiches a SAP layer between two hydrophilic sheets or the like. Further, the absorbent member may be formed in an hour-glass shape or a rectangular shape.

In the above-mentioned embodiment, with respect to specific materials used for forming the connecting member 3, the stretchable elastic members 10, 10', 11, the base sheet of the adjusting tape 13, the target sheet 16, the reinforcing sheet 17, the top sheet 21, the back sheet 22 and the like, it must be noted that the present invention is not limited to these constitutional materials at all.

Figure 7:
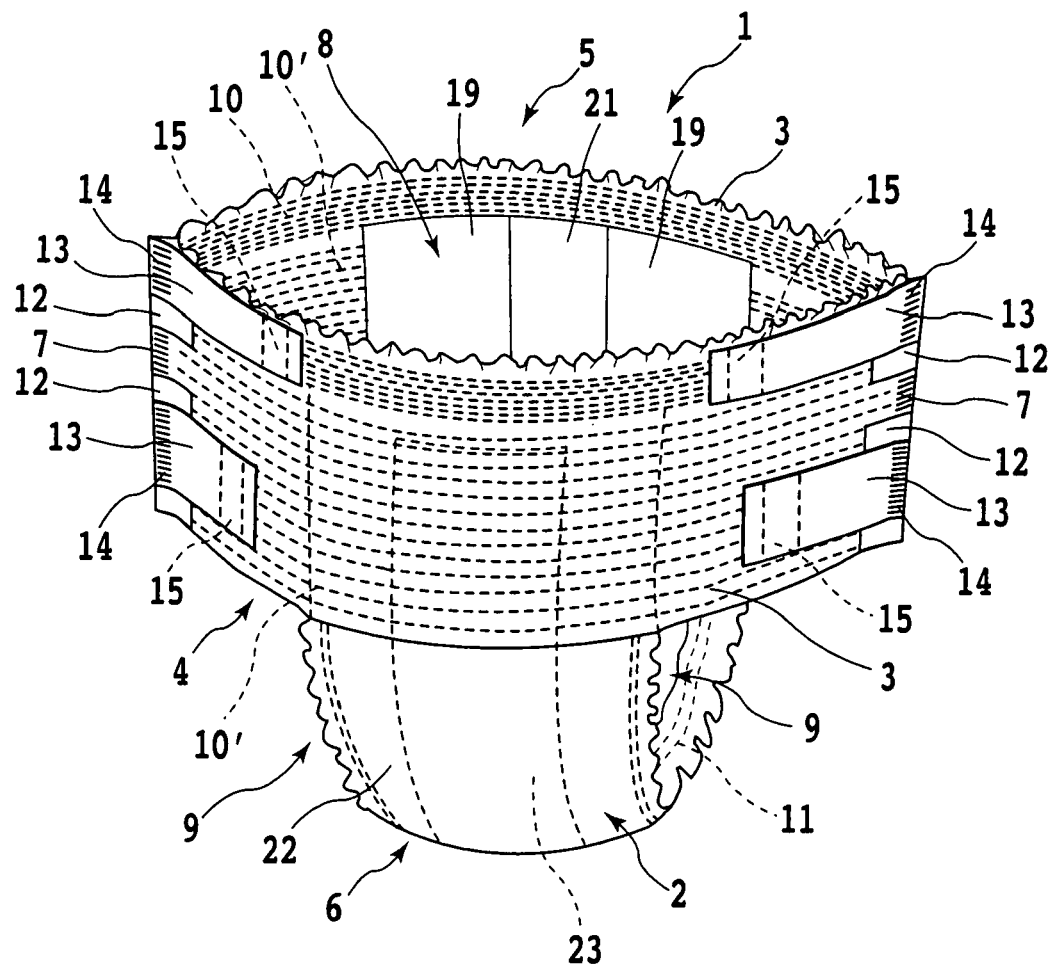
FIG. 7 is a perspective view of a disposable pant-type diaper of another embodiment of the present invention as viewed from a front portion side.

FIG. 7 is a perspective view of a disposable pant-type diaper of another embodiment of the present invention as viewed from a front portion side, wherein parts identical with the parts shown in FIG. 1 are indicated by the same symbols and the repeated explanation is omitted.

In this embodiment, in both side-edge portions of the connecting member 3 on the front portion 4 side, at two regions consisting of a region which contains an upper side on the waist opening 8 side and a region which contains a lower side on the leg opening 9 side, cutout portions 12 are formed respectively, and adjusting tapes 13 are attached on portions where these cutout portions 12 are formed.

Figure 8:
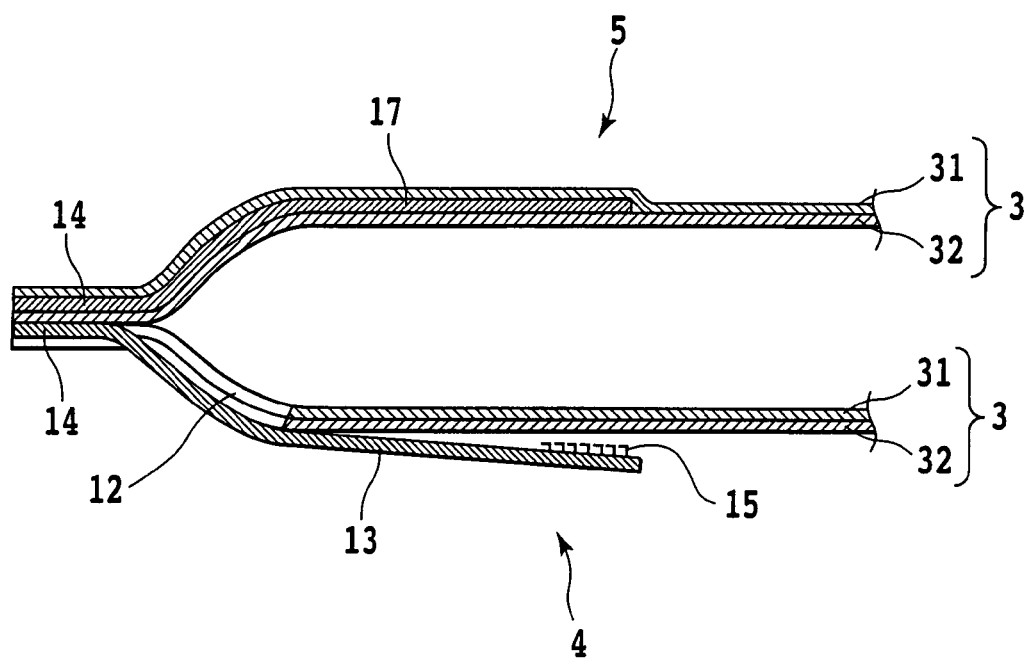
FIG. 8 is a cross-sectional view of a disposable pant-type diaper of another embodiment of the present invention similar to FIG. 4.

FIG. 8 is a cross-sectional view of a disposable pant-type diaper of another embodiment of the present invention showing a cross section similar to the cross section shown in the preceding FIG. 4. In FIG. 8, parts identical with the parts shown in FIG. 4 are indicated by the same symbols and the repeated explanation is omitted.

In FIG. 8, a reinforcement sheet 17 is arranged between two sheets of non-woven fabrics 31, 32 which form a connecting member 3 on a back portion 5 side.

A hook elements as a fastening means 15 provided to the free end of an adjusting tape 13 is directly and detachably fastened on the surface of the connecting member 3 on a front portion 4 side. That is, the connecting member 3 in this embodiment also serves as a target sheet 16.

The disposable pant-type diaper of the present invention may include a main body which is formed of a liquid permeable top sheet, a liquid impermeable back sheet, and an absorbent member which is arranged between the both sheets, and side panels attached on both longitudinal side-edge portions of front and back portions of the main body, and the main body is formed into a panties shape by joining both side-edge portions of the side panels which face each other.

In this case, the side panels may be formed by a thermal adhesiveness non-woven fabric made of synthetic fibers which use a thermoplastic resin such as polyethylene, polypropylene, polyester or other resin as a raw material. A stretchable elastic member such as a stretching film, a stretching net, flat rubber, string rubber, a stretchable foamed body or the like which is in a stretched state is adhered and fixed to the front portion using a hot melt adhesive agent. Alternatively, a side panel which is formed by sandwiching and fixing a sheet between the non-woven fabrics by thermal adhesiveness may be used. Further, a sheet which is made stretchable by sandwiching a stretchable elastic member using non-woven fabrics which are stretchable while holding a natural length can be also used.

A disposable pant-type diaper of the present invention may be a diaper which includes a liquid permeable top sheet, a liquid impermeable back sheet, an absorbent member having an absorbent which is arranged between the both sheets, and an outer member on which the absorbent member is mounted and which holds the absorbent member by bringing the absorbent member into contact with a wearer, and both side-edge portions of a front portion and a back portion of the outer member which face each other are joined to each other thus forming the diaper into a panties shape.

In this case, the outer member may be formed of a non-woven fabric made of synthetic fibers which use a thermoplastic resin such as polyethylene, polypropylene, polyester or the like. The non-woven fabrics may be used in a single form or by laminating several kinds of non-woven fabrics.

The present invention has been described in detail with respect to preferred embodiments, and it will now be apparent from the foregoing to those skilled in the art that changes and modifications may be made without departing from the invention in its broader aspect, and it is the intention, therefore, in the apparent claims to cover all such changes.

The invention claimed is:

1. A disposable pant-type diaper comprising a front portion, a back portion, and a crotch portion which is positioned between the front and back portions, in which a waist opening and a pair of leg openings are formed by joining both longitudinal side-edge parts of the front and back portions which face each other, and a stretchable elastic member is disposed along at least a part of each opening, wherein
   a cutout portion is formed in a part of the side-edge part of one of the front and back portions so that only the front and back portions assume a non-joining state at the side-edge part on which the cutout portion is formed, and wherein
   an adjusting tape is arranged on the cutout portion so that one end part of the adjusting tape is attached on a non-joining part of the side-edge part of one of the front and back portions without the cutout portion formed therein, the non-joining part on which the one end of the adjusting tape is attached being exposed by forming the cutout portion, the other end region of the adjusting tape having fastening means detachably fastened to one of the front and back portions on which the cutout portion is formed.

2. A disposable pant-type diaper as claimed in claim 1, wherein a base of the adjusting tape is formed of a material having a stretchable elasticity.

3. A disposable pant-type diaper as claimed in claim 1, wherein the diaper comprises a main body including a liquid permeable top sheet, a liquid impermeable back sheet, and an absorbent member which is arranged between the both sheets, the diaper being formed into a panties shape by joining both side-edge parts of the front and back portions which face each other.

4. A disposable pant-type diaper as claimed in claim 3, wherein side panels are attached on both side-edge parts of the front and back portions of the main body, and the side panels being joined to each other so that the main body is formed into the panties shape.

5. A disposable pant-type diaper as claimed in claim 4, wherein the side panels are formed of a material having a stretchable elasticity.

6. A disposable pant-type diaper as claimed in claim 1, wherein the diaper comprises
   a main absorbent body having a liquid permeable top sheet, a liquid impermeable back sheet, and an absorbent member which is arranged between the both sheets; and
   a belt-like connecting member which is arranged on the front and back portions of the main absorbent body and has a length which allows the connecting member to extend to the outside from both side-edge parts of the main absorbent body, and wherein
   both side-edge parts of the connecting member which face each other along the longitudinal direction of the diaper are joined so that the diaper is formed into a panties shape.

7. A disposable pant-type diaper as claimed in claim 6, wherein the belt-like connecting member is formed of a material having a stretchable elasticity.

8. A disposable pant-type diaper as claimed in claim 1, wherein the diaper comprises
   a main absorbent body having a liquid permeable top sheet, a liquid impermeable back sheet, and an absorbent member which is arranged between the both sheets; and
   an outer member on which the main absorbent body is attached and holds the main absorbent body so that the main absorbent body is brought into contact with a wearer, and wherein
   both side-edge parts of the front and back portion of the outer member which face each other are joined so that the diaper is formed into a panties shape.

9. A disposable pant-type diaper as claimed in claim 2 wherein the diaper comprises a main body including a liquid permeable top sheet, a liquid impermeable back sheet, and an absorbent member which is arranged between the both sheets, the diaper being formed into a panties shape by joining both side-edge parts of the front and back portions which face each other.

10. A disposable pant-type diaper as claimed in claim 9, wherein side panels are attached on both side-edge parts of the front and back portions of the main body, and the side panels being joined to each other so that the main body is formed into the panties shape.

11. A disposable pant-type diaper as claimed in claim 10, wherein the side panels are formed of a material having a stretchable elasticity.

12. A disposable pant-type diaper as claimed in claim 2, wherein the diaper comprises
- a main absorbent body having a liquid permeable top sheet, a liquid impermeable back sheet, and an absorbent member which is arranged between the both sheets; and
- a belt-like connecting member which is arranged on the front and back portions of the main absorbent body and has a length which allows the connecting member to extend to the outside from both side-edge parts of the main absorbent body, and wherein
- both side-edge parts of the connecting member which face each other along the longitudinal direction of the diaper are joined so that the diaper is formed into a panties shape.

13. A disposable pant-type diaper as claimed in claim 12, wherein the belt-like connecting member is formed of a material having a stretchable elasticity.

14. A disposable pant-type diaper as claimed in claim 2, wherein the diaper comprises
- a main absorbent body having a liquid permeable top sheet, a liquid impermeable back sheet, and an absorbent member which is arranged between the both sheets; and
- an outer member on which the main absorbent body is attached and holds the main absorbent body so that the main absorbent body is brought into contact with a wearer, and wherein
- both side-edge parts of the front and back portion of the outer member which face each other are joined so that the diaper is formed into a panties shape.

* * * * *